(12) United States Patent
Nuttall et al.

(10) Patent No.: US 6,987,168 B1
(45) Date of Patent: Jan. 17, 2006

(54) TRYPTASE INHIBITOR PROTEINS DERIVED FROM BLOOD-FEEDING ANTHROPOD ECTOPARASITES

(75) Inventors: Patricia Anne Nuttall, Oxon (GB); Guido Christiaan Paesen, Jericho (GB)

(73) Assignee: Evolutec Limited, Reading (GB)

( * ) Notice: Subject to any disclaimer, the term of this patent is extended or adjusted under 35 U.S.C. 154(b) by 358 days.

(21) Appl. No.: 10/031,685

(22) PCT Filed: Jul. 19, 2000

(86) PCT No.: PCT/GB00/02791

§ 371 (c)(1),
(2), (4) Date: Apr. 3, 2002

(87) PCT Pub. No.: WO01/05823

PCT Pub. Date: Jan. 25, 2001

(30) Foreign Application Priority Data

Jul. 19, 1999 (GB) .................................. 9916913

(51) Int. Cl.
*C07K 1/00* (2006.01)
*C07K 14/00* (2006.01)
*C07K 17/00* (2006.01)

(52) U.S. Cl. ..................................... 530/350
(58) Field of Classification Search ................ 530/350
See application file for complete search history.

(56) References Cited

U.S. PATENT DOCUMENTS 6,248,329 B1 * 6/2001 Chandrashekar et al. 424/191.1

OTHER PUBLICATIONS

Elrod,K., et al., Am J Respiratory critical Care Medicine, 1997, vol. 156, pp. 375-381.*
Katunuma, NADV.Enzyme Regul. 1990, vol. 30, pp. 377-392.*
Mikayama et al. PNAS, 1993. 90: 10056-10060.*
Burgess et al J Cell Biol. 111:2129-2138, 1990.*
Lazar et al. Mol Cell Biol. 8:1247-1252, 1988.*
Attwood Science 2000; 290:471-473.*
Skolnick et al. Trends in Biotech. 2000; 18(1):34-39,.*
Metzler et al. Nature Structural Biol. 1997; 4:527-531.*
Ngo et al, iThe Protein Folding Problem and Tertiary Structure Prediction, 1994. (ed.), Birkhauser, Boston, MA, pp. 433 and 492-495.*
Ellis, R.W. Chapter 29 of "VACCINES" Plotkin, S.A. et al. (eds) published by W. B. Saunders company (Philadelphia) in 1988, especially p. 571.*

* cited by examiner

*Primary Examiner*—Christina Chan
*Assistant Examiner*—Michail A. Belyavskyi
(74) *Attorney, Agent, or Firm*—Klauber & Jackson

(57) ABSTRACT

The present invention relates to novel protease inhibitor proteins that have been identified in ticks. These proteins may be used as components of vaccines, as inhibitors of mast cell tryptase, in detection of mast cells and in the isolation and purification of mast cell tryptase. The invention also relates to the control of diseases and injury caused by parasites in animals and humans and to the use of the proteins of the invention in the treatment of certain diseases and allergies.

10 Claims, 6 Drawing Sheets

FIG. 1

```
T3→
    GAAACCTCATGGGCCGACTACCCTAATCGTCGCCATGTGCTGTGGCTTCGTTGCAAGCACACTAGG    70
                                      M  G  R  T  T  L  G
                      P1→
    AAATGCCTACCCTAAAGTGGAAGAAAGACGTAACAGGCCTAATTGGGATTTTGGGAAAAGAAGAAGAG   140
     N  A  Y  P  K  V  E  E  R  R  N  R  P  N  W  D  F  G  K  R  K  E  E
                                                                        *

TGTACCGTTCCTATTGGTTGAGAGCGAACCAGTAAAAGGGCTTGCAAGGCTAGATTTACTAGTATTACT   210
     C  T  V  P  I  G  W  S  E  P  V  K  G  L  C  K  A  R  F  T  R  Y  Y  C
         S1→                                              ←S2
    GCATGGGGAACTGTGTGCAAGGTATACGAAGGCTGCTACACAGGAGGCTATTCCAGAATGGTGAATGCGC   280
     A  M  G  N  C  C  K  V  Y  E  G  C  Y  T  G  G  Y  S  R  M  G  E  C  A
                                                                ←P2
    GAGAAATTGTCCCGGCTTCAAAAGACCTCCGGTTCAGGAGAACGGACTAGAGAGAACGGAACA        350
     R  N  C  P  G  F  K  R  P  T  P  G  F  R  P  R  H  G  L  E  N  G  T

GAGCCTGGACCTTGAAACCTCAGATAATAATTCTCCGAAGACCTCGATTATTTCACCATGAGGCCGTTTT   420
     E  P  G  P  *
                                                                    ←T7
    TTTTTCCACAATAAAAGCGGACAAGGAGAGAACATACATCATACTGAAATAAAAATAAGAAACCAAAAAAAAAA   490
```

FIG. 3

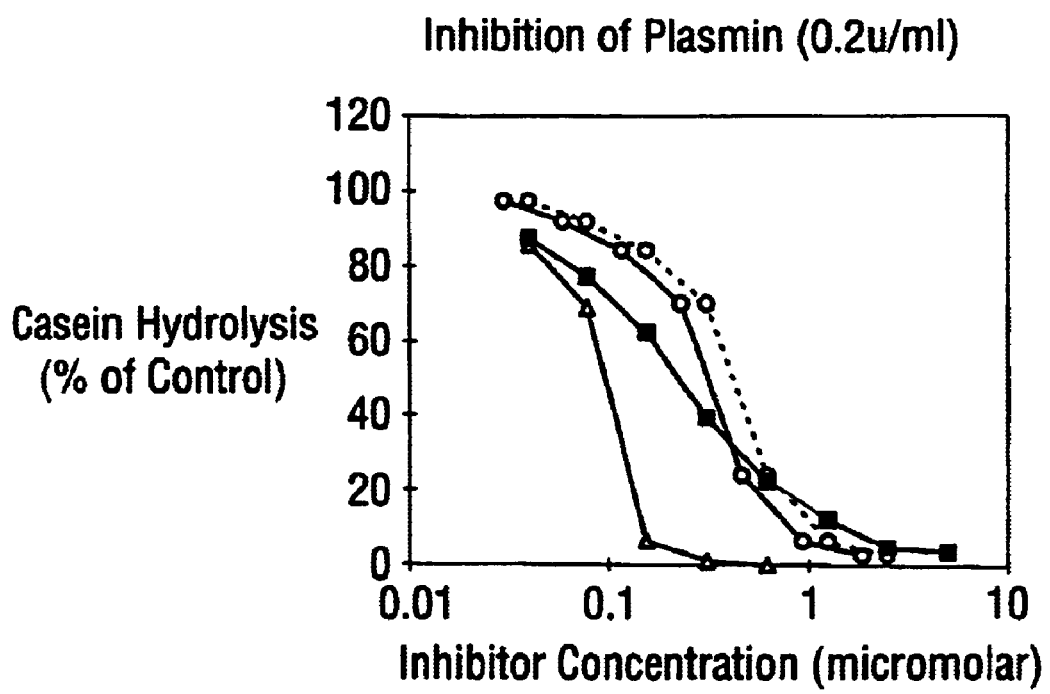
FIG. 5
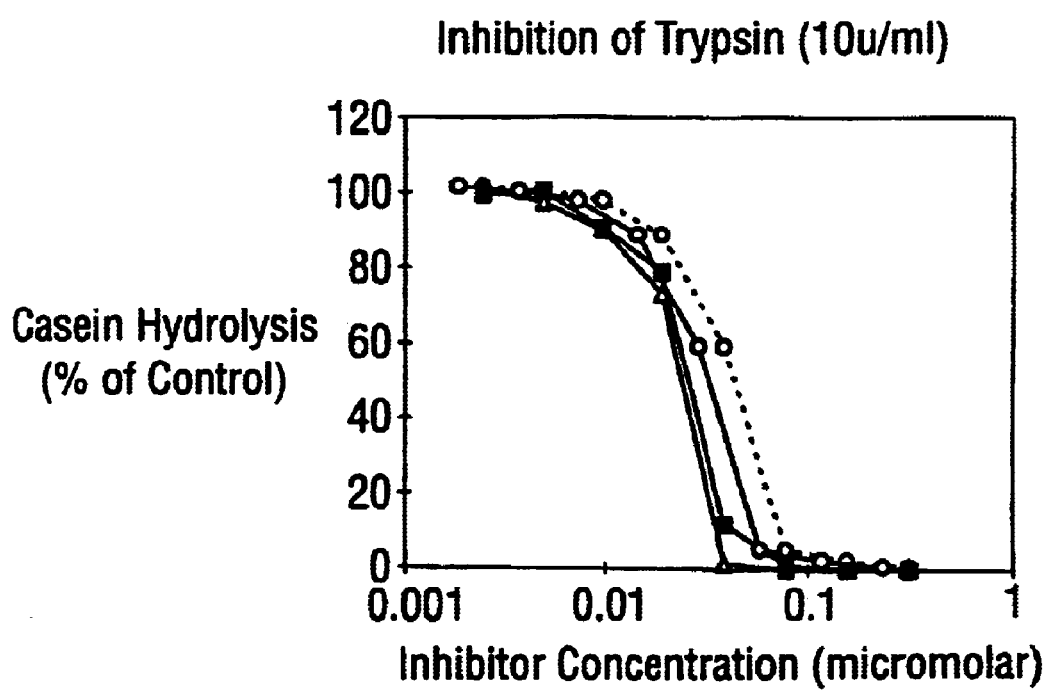

TRYPTASE INHIBITOR PROTEINS DERIVED FROM BLOOD-FEEDING ANTHROPOD ECTOPARASITES

The present invention relates to novel proteins that have been identified in ticks. These proteins may be used a components of vaccines, as inhibitors of mast cell tryptase (hereafter referred to as MCT), in the detection of mast cells and in the isolation and purification of MCT. The invention also relates to the control of diseases and injury caused by parasites in animals and humans and to the use of the proteins of the invention in the treatment of diseases and allergies.

All documents mentioned in the text and listed at the end of this description are incorporated herein by reference.

Human MCT is an endoprotease that is stored in the secretory granules of mast cells and, upon activation, is released from the mast cells as a tetramer that is stabilised by heparin. Removal of heparin leads to the dissociation of the tryptase complex into enzymatically inactive monomers (Schwartz, 1994).

Tryptase is the principal protein mediator component of human mast cell granules, accounting for over 20% of the total cellular protein (Schwartz, 1994). MCT is a specific marker of mast cells, allowing for their differentiation from basophils.

Mast cells are found in many tissues but are present in greater numbers along the epithelial linings of the body, such as the skin, respiratory tract and gastrointestinal tract. Mast cells are often located in the proximity of small blood vessels. They are involved in a variety of physiological and pathophysiological states, including acute inflammation, immediate hypersensitivity, delayed-type hypersensitivity, cell growth regulation, defense against neoplasia and the sensation of pain and itch (Liang et al, 1998). Mast cells are also implicated in chronic inflammatory states and are involved in neuroimmune interactions (Leon et al., 1994).

Mast cell tryptase is an important inflammatory response mediator. Experiments (mainly performed in vitro) suggest it plays important roles in diseases such as asthma, psoriasis, interstitial lung disease, rheumatoid arthritis, gingivitis and periodontitis. Mast cell tryptase has also been implicated in tumorigenesis and angiogenesis, due to its potential to activate pro-urokinase and the matrix metalloproteinase pro-stromelysin. Tryptase-like enzymes have also been described to take part in the activation and internalisation of pathogenic viruses, such as influenza virus, Sendai virus and human immunodeficiency virus (Pohlig et al., 1996).

Human tryptase is inhibited by small molecular weight substances (e.g. leupeptin and diisopropyl fluorophosphate). Divalent cations, such as calcium, and benzamidine and its derivatives are competitive inhibitors of human mast cell tryptase (Schwartz, 1994). However, human tryptase, unlike most other serine esterases, is not inhibited by classical inhibitors of serine proteases, such as aprotinin and soybean trypsin inhibitor. Endogenous inhibitors that target the catalytic sites of mast cell tryptase have yet to be reported. Human tryptase activity is inhibited by lactoferrin and myeloperoxidase (both neutrophil-derived) and by anti-thrombin-III, all of which antagonise the glycosaminoglycans (heparin or chondroitin sulfate) that stabilise the MCT tetramer (Alter et al., 1990; Cregar et al., 1999; Elrod et al., 1997).

A leech-derived inhibitor of human tryptase (LDPI) has been previously described. A recombinant form of this Kazal-type protein has been found to inhibit efficiently 2 of the 4 catalytic sites of the tetrameric tryptase (Stubbs et al., 1997; Auerswald et al., 1994; Muhlhahn et al., 1994; Sommerhoff et al.,1994).

Due to the known importance of MCT in mammalian disease and in the allergic response, there is a clear need for highly specific and effective inhibitors of this protein. A novel protein has now been discovered in a tick species that is capable of inhibiting the activity of human mast cell tryptase.

SUMMARY OF THE INVENTION

According to a first aspect of the present invention there is provided a recombinant protein that exhibits significant sequence homology with the tick-derived protease inhibitor protein (TdPI) sequence given in FIG. 1 (SEQ.ID. NO:2), an active fragment of said protein or a functional equivalent of said protein.

As used herein, the term "significant sequence homology" is meant to include all proteins that share a common function with TdPI and that exhibit common sequence homology or homology between motifs that are present in the polypeptide sequences. "Significant" overall homology refers to 50% or more of the amino acids in the sequence being completely conserved as identical residues if the homologous protein is aligned with the sequence of TdPI. Preferably, the alignments are obtained using GCG's bestfit command (gap creation penalty=2.5; gap extension penalty=0.5)(Genetics-Computer-Group, 1994).

Preferably, the degree of homology is at least 60% across the entire length of the protein. More preferably, the degree of homology is at least 70%, even more preferably 75%, most preferably 80% or more.

Included in this aspect of the invention there is provided a protein comprising the sequence identified herein as tick-derived protease inhibitor protein (TdPI), an active fragment thereof or a functional equivalent thereof. This sequence is given in accompanying FIG. 1 (SEQ.ID.NO:2). This protein was identified as being encoded by a cDNA from a tick salivary gland library. The protein has a molecular weight of approximately 13.5 kDa and appears to belong to the family of Kunitz-type protease inhibitors. The sequence similarity with other members of this family such as aprotinin and inter-alpha-trypsin inhibitor is low, but the putative reactive centre and the position of the cysteines is to some extent conserved.

The term "functional equivalent" is used herein to describe proteins that have an analogous function to the TdPI protein, either in inhibiting tryptase or in possessing one or more epitopes that can be used in the development of vaccines that target proteins that exhibit significant sequence homology with TdPI. The term "functional equivalent" also refers to molecules that are structurally similar to the TdPI protein identified herein or that contain similar or identical tertiary structure. This term also includes protein fragments that retain the ability to inhibit tryptase, preferably human mast cell tryptase.

The analogous function in inhibiting tryptase is preferably directed against the catalytic activity of tryptase, preferably mast cell tryptase more preferably human mast cell tryptase, is characterised by a Ki of less than 1 $\mu$M, more preferably 100 nM, even more preferably 20 nM, even more preferably less than 10 nM, most preferably less than 1 nM, as assessed using any standard tryptase inhibition assay, such as that described herein (see section entitled "Protease inhibitions assays" in the Examples below).

Alternatively, or in addition to possessing inhibitory activity against tryptase, "functional equivalent" is used herein to describe proteins that contain epitopes which can be used in the development of vaccines against the proteins of the inventions. Such functional equivalents, and also fragments containing suitable epitopes, may be used to develop vaccines directed against blood-feeding parasites, that target members of the UPI protein family. Functional equivalents may of course be made more or less immunogenic than the corresponding wild type protein or protein fragment in order to suit a desired application. By "wild type" is meant the naturally-occurring genotype that is characteristic of most members of a species. If the proteins are to be used in a vaccination regime to induce host resistance to parasite proteins, then the molecules may be modified so as to enhance their immunogenicity. They will thus be more likely to elicit an immune response in the vaccinated host. Functional equivalents of the proteins of the invention will include single or multiple amino-acid substitution(s), addition(s), insertion(s) and/or deletion(s) from the wild type protein sequence and substitutions of chemically-modified amino acids that do not affect the function or activity of the protein in an adverse manner. This term is also intended to include natural biological variants (e.g. allelic variants or geographical variations within all the different species from which the wild type proteins are derived).

"Active" fragments are those that either inhibit tryptase, preferably human mast cell tryptase, and/or contain one or more epitopes that can be used in the development of vaccines against the proteins of the present invention. These biological properties are described above.

Preferably, the proteins of this aspect of the invention are derived from blood-feeding ectoparasites, such as mosquitoes or leeches, or from venomous animals such as spiders, scorpions or snakes. More preferably, the proteins are derived from ticks, most preferably Ixodid ticks such as *Rhipicephalus appendiculatus*.

According to a second aspect of the invention there is provided a recombinant protein derived from a blood-feeding arthropod ectoparasite that inhibits tryptase, an active fragment thereof, or a functional equivalent thereof. Preferably, the recombinant protein is derived from a tick, most preferably an Ixodid tick such as *Rhipicephalus appendiculatus*. The activity of these molecules in inhibiting the catalytic activity of tryptase, preferably mast cell tryptase, more preferably human mast cell tryptase, is characterised by a Ki of less than 1 $\mu$M, more preferably 100 nM, more preferably 20 nM, even more preferably less than 10 nM, most preferably 1 nM or less.

Derivatives of the proteins of the above-described aspects of the invention are included as embodiments of the invention. Such derivatives may include an additional protein or polypeptide fused at its amino- or carboxy-terminus or added internally. The purpose of the additional polypeptide may be to aid detection, expression, separation or purification of the protein or may be to lend the protein additional properties as desired. Examples of potential fusion partners include β-galactosidase, glutathione-S-transferase, luciferase, a polyhistidine tag, a T7 polymerase fragment and a secretion signal peptide.

The proteins of the present invention can be prepared using known techniques of molecular biology and protein chemistry. Protein fragments may be prepared by chemical synthesis, a technique that is especially useful for the generation of short peptides derived from the full length protein sequence, for use as immunogens.

The proteins of the invention may be prepared in recombinant form by expression in a host cell. Such expression methods are well known to those of skill in the art and many are described in detail by Sambrook et al, 1989, and Fernandez & Hoeffler, 1998.

A third aspect of the invention provides for the use of the proteins, protein fragments and functional equivalents of the invention to inhibit a tryptase, such as mast cell tryptase, in mammals, thereby to regulate its action and to control its pathological effects. Such molecules may also be used to inhibit trypsin, plasmin and, to a lesser degree, tissue kallikrein.

The invention also includes the use of the above-described proteins, protein fragments and functional equivalents as anti-inflammatory agents. Preferably, these molecules are provided as a pharmaceutical composition including an inert carrier. The protein, protein fragment or functional equivalent may constitute the sole active component of the composition or can form part of a therapeutic package, such as a component of creams for topical administration to insect, snake or scorpion bites, or to skin affected by dermatitis. It may also be used as a carrier molecule for tryptase and tryptase-related compounds, in creams, oils, powders or pills, to provide slow release of the bound components.

The invention also comprises the use of the proteins, protein fragments and functional equivalents of the invention for the quantification of tryptase levels, preferably human mast cell tryptase levels, for example, in blood, nasal lavage fluid, tissues or food products. This may be as part of a kit that comprises one or more proteins, protein fragments or functional equivalents of the invention, together with means of detection (for example radiolabeled tryptase, antibodies, enzymes such as alkaline phosphatases, peroxidases and luciferases) that allow the accurate quantification of tryptase in the sample to be tested. Such kits may resemble radioimmunoassay or ELISA kits, with the proteins of the invention acting as binding molecules, rather than antibodies directed against tryptase or against tryptase-related molecules. One aspect of the present invention comprises such kits incorporating the molecules of the present invention.

The proteins, protein fragments and functional equivalents of the invention can also be used for the detection of cells carrying tryptase, and in particular for the detection of mast cells. Any technique common to the an may be used in such a detection method and may comprise immunocytochemical and histological techniques, in which the protein, protein fragment or functional equivalent is used in combination with antisera (such as anti-TdPI antisera), or in which the molecule is directly coupled to a label or dye, such as FITC. An entire protein may be used, or simply an active binding fragment in order to detect substrate. In another embodiment, the wild type protein may be fused either genetically or synthetically to another protein such as an alkaline phosphatase, luciferase or peroxidase in order to facilitate its detection. Other methods to detect tryptase-containing cells or samples may involve blotting techniques (Towbin et at, 1979), gel retardation, affinity chromatography, or any of the other suitable methods that are used in the art.

The invention also comprises the use of the proteins, protein fragments and functional equivalents of the present invention bound to a support to remove, purify, isolate or extract tryptase, for instance from body tissues, blood or food products. The support may comprise any suitable inert material and includes gels, magnetic and other beads, microspheres, binding columns and resins.

The present invention also includes the use of the proteins, protein fragments and functional equivalents of the invention as tools in the study of inflammation, inflammation-related processes or other physiological processes involving tryptase. These molecules may also be used as tools to study further the characteristics and functions of MCT itself. For example, the molecules may be used for tryptase inhibition or depletion in cell cultures or in inflamed animal tissues, in order to study the importance of tryptase in these systems.

Metazoan parasites, particularly arthropods and helminths, are also sources of infectious diseases and other injurious effects that have major impacts in human and veterinary medicine. Control of arthropod and helminth parasites currently relies primarily on the use of chemicals such as acaricides and antihelmintics. Attempts have been made to use immunological means of control through the use of vaccine technology. There has been some success in identifying certain protective antigens as potential vaccine candidates, but only a few have as yet come to commercial fruition, most notably for the cattle lungworm *Dictyocaulus viviparous* and the cattle tick *Boophilus microplus*. Despite these developments, there is a continuing need for metazoan parasite vaccines and in particular for a vaccine which may be used across a broad range of arthropod and/or helminth genera.

The present invention therefore also provides for the use of the proteins, protein fragments and functional equivalents of the invention as immunogens for use as metazoan parasite vaccines and in particular as protective immunogens in the control of diseases caused by arthropod and other metazoan parasites. Suitable candidates for vaccination include domesticated animals such as cattle, goats, sheep, dogs, cats and other animals which require protection against metazoan parasites, especially ticks. The vaccine may include certain compounds for use as adjuvants. Suitable adjuvants are well known in the art and include oil-in-water emulsion formulations, saponin adjuvants, Complete Freund's Adjuvant (CFA) and Incomplete Freund's Adjuvant (IFA), cytokines, and other substances that act as immunostimulating agents to enhance the effectiveness of the composition.

According to a still further aspect of the present invention, there is provided a method of vaccinating a mammal against a disease or condition, comprising administering to a mammal a protein, protein fragment or functional equivalent according to the above-described aspects of the invention whose expression is associated with the disease or condition.

A further aspect of the invention provides a method of treating a mammal suffering from a disease or a condition such as asthma, psoriasis, an interstitial lung disease, rheumatoid arthritis, gingivitis, periodontitis, an allergic reaction, cancer or any other tryptase-mediated condition, comprising administering to said mammal a protein, protein fragment or functional equivalent according to the above-described aspects of the invention in a therapeutically-effective amount, optionally in conjunction with a pharmaceutically-acceptable carrier.

According to a further aspect of the present invention there is provided an immunogenic composition comprising a protein, protein fragment or functional equivalent of the above-described aspects of the invention in conjunction with a pharmaceutically-acceptable carrier.

Pharmaceutically-acceptable carriers include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, lipid aggregates (such as oil droplets or liposomes) and inactive virus particles. Such carriers are well known to those of skill in the art. The composition may be used as a vaccine and may thus optionally comprise an immunostimulating agent (adjuvant) for instance an adjuvant as referred to above. According to a further aspect of the invention, there is provided a process for the formulation of a vaccine composition comprising bringing a protein, protein fragment or functional equivalent according to the above-described aspects of the invention into association with a pharmaceutically-acceptable carrier, optionally with an adjuvant.

According to a further aspect of the invention there is provided a nucleic acid molecule comprising a nucleotide sequence encoding a protein, protein fragment or functional equivalent of the above-described aspects of the invention. Such molecules include single- or double-stranded DNA, cDNA and RNA, as well as synthetic nucleic acid species. Preferably, the nucleic acid sequences comprise DNA.

A cDNA encoding TdPI is disclosed herein by way of example and its sequence and the amino acid sequence it encodes are shown in FIG. 1 (nucleotides (SEQ ID NO:1) and amino acids (SEQ ID NO:2) are given in their standard one letter abbreviations).

A preferred nucleic acid molecule according to the invention comprises a nucleotide sequence identical to or complementary to the sequence shown in FIG. 1 (SEQ ID NO:1), or a sequence that is degenerate or substantially homologous therewith, or which hybridises with this sequence under non-stringent conditions, for instance 6×SSC/50% formamide at room temperature, and washed under conditions of low stringency, for instance (2×SSC room temperature or 2×SSC, 42° C. or, more preferably, binding under conditions of higher stringency, e.g. 2×SSC, 65° C. (SSC=0.15M NaCl, 0.015M sodium citrate, pH 7.2).

Preferably, said nucleic acid sequences display at least 60% identity to the cDNA encoding TdPI, or DNA sequences of which the translation product (either a partial stretch or the complete translation product) displays at least 60% or more identity with the TdPI sequence, when aligned, preferably using GCG'S bestfit command (gap creation penalty= 2.5; gap extension penalty=0.5) (Genetics Computer Group, 1994).

The invention also includes cloning and expression vectors containing the DNA sequences of this aspect of the invention. Such expression vectors may incorporate the appropriate transcriptional and translational control sequences, for example enhancer elements, promoter-operator regions, termination stop sequences, mRNA stability, sequences, start and stop codons or ribosomal binding sites, linked in frame with the nucleic acid molecules of the invention.

Additionally, it may be convenient to cause the recombinant protein to be secreted from certain hosts. Accordingly, further components of such vectors may include nucleic acid sequences encoding secretion signalling and processing sequences.

Vectors according to the invention include plasmids and viruses (including both bacteriophage and eukaryotic viruses), as well as other linear or circular DNA carriers, such as those employing transposable elements or homologous recombination technology. Many such vectors and expression systems are well known and documented in the art (Fernandez & Hoeffler, 1998). Particularly suitable viral vectors include baculovirus-, adenovirus- and vaccinia virus-based vectors.

Suitable hosts for recombinant expression include commonly-used prokaryotic species, such as *E. coli*, or eukaryotic yeasts that can be made to express high levels of recombinant proteins and that can easily be grown in large quantities. Mammalian cell lines grown in vitro are also suitable, particularly when using virus-driven expression systems. Another suitable expression system is the baculovirus expression system that involves the use of insect cells as hosts. An expression system may also constitute host cells that have the encoding DNA incorporated into their genome. Proteins, or protein fragments may also be expressed in vivo, for example in insect larvae or in mammalian tissues.

A variety of techniques are known and may be used to introduce the vectors according to the present invention into prokaryotic or eukaryotic cells. Suitable transformation or transfection techniques are well described in the literature (Sambrook et al, 1989; Ausubel et al., 1991; Spector, Goldman & Leinwald, 1998). In eukaryotic cells, expression systems may either be transient (e.g. episomal) or permanent (chromosomal integration) according to the needs of the system.

Nucleic acid molecules according to the present invention may also be used to create transgenic animals, particularly rodent animals. This may be done locally by modification of somatic cells, or by germ line therapy to incorporate heritable modifications.

The invention also includes transformed or transfected prokaryotic or eukaryotic host cells, or transgenic organisms containing a nucleic acid molecule as defined above.

A further aspect of the invention provides a method for preparing a protein, protein fragment of functional equivalent of the invention, as defined above, which comprises culturing a host cell containing a nucleic acid molecule according to the invention under conditions whereby said protein is expressed and recovering said protein thus produced.

Various aspects and embodiments of the present invention will now be described in more detail by way of example, with particular reference to a protein isolated from the tick, *Rhipicephalus appendiculatus*. It will be appreciated that modification of detail may be made without departing from the scope of the invention.

BRIEF DESCRIPTION OF FIGURES

FIG. 1 shows the cDNA sequence (SEQ ID NO:1) and inferred amino-acid sequence (SEQ ID NO:2) of TdPI-encoding clone 76-3.

FIG. 3 shows an alignment of TdPI (SEQ ID NO:2) with Kunitz domains of the bovine colostrum trypsin inhibitor (SEQ ID NO:3)(BovCol: Cechova, 1976), (bovine) aprotinin (SEQ ID NO:5) (Creighton & Charles, 1987), and the rat tissue factor pathway inhibitor (TFPI-2 (SEQ ID NO:4); only the second, factor Xa-inhibiting domain is shown; Enjyoji et al., 1992).

FIG. 5 shows the activities of plasmin (left) and trypsin (right) in the presence of increasing amounts of rTdPI as determined by measuring peptide release from resorufin-labelled casein.

EXAMPLES

Ticks

Figure 2:
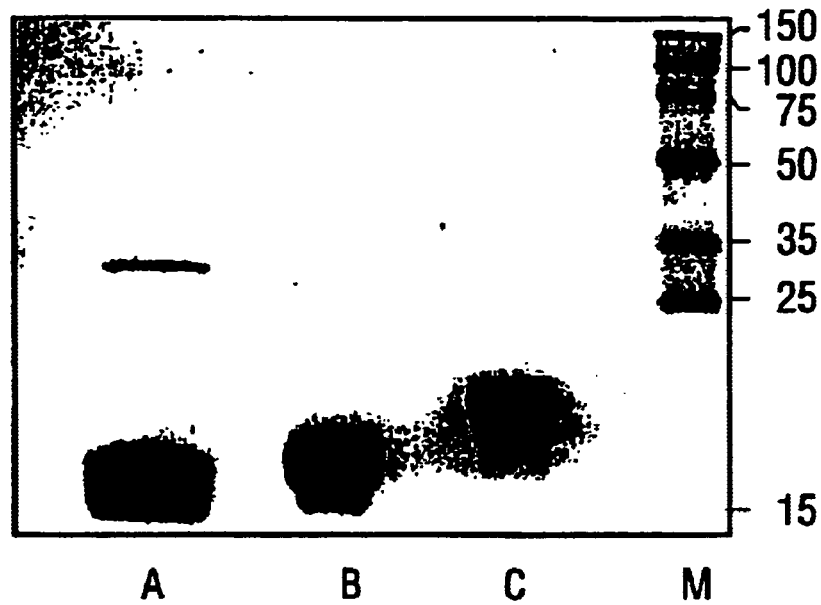
FIG. 2 shows a 15% SDS-polyacrylamide gel showing rTdPI, purified by means of metal-affinity chromatography and cation exchange.

Ticks were reared according to Jones et al., 1988. All three developmental stages of *R. appendiculatus* were fed on Dunkin Hartley guinea pigs. When not feeding, all ticks were maintained at 21 to 26° C. and 85% relative humidity.

cDNA

Clone 76, containing the TdPI cDNA, was one of several clones randomly picked from a *R. appendiculatus* salivary gland expression library in Lambda Zap II (Stratagene), which was constructed with mRNA from ticks that had been feeding on Dunkin Hartley guinea pigs for 2 days (Paesen & Nuttall, 1996). Phagemid was excised in vivo and used to generate double-stranded pBluescript SK(-) plasmid in XL1-Blue cells (Short et al., 1988). Plasmid was purified from overnight cultures (Geode & Feinstein, 1992) and alkali-denatured (Mierendorf & Pfeffer, 1987) before sequencing according to Sanger & Coulson, 1975.

The complete sequences of both the plus and minus strand of the 76-3 insert were determined. The forward primer (S1→) (corresponding with nucleotides 209 to 224), reverse primer (←S2) (annealing to nucleotides 255 to 271) and the plasmid-specific T3 (T3→) and T7 (←T7) primers (insert-specific primer sequences, or their annealing sites, are underlined) are shown in FIG. 1. P1→ and P2← denote the primer sites used in the RT-PCR experiment.

The sequence obtained by N-terminal sequencing of the rTdPI protein is in bold italics in FIG. 1. The wave denotes a heparin-binding consensus sequence. The double line indicates a putative glycosylation site. The polyadenylation signal and the polyA-tail are shown in bold letter type. The leucine indicated by the asterisks is a methionine in clones 76, 76-1 and 76-2.

Sequence data were analysed using the GCG sequence analysis software (Genetics-Computer-Group, 1994 #4). Protein database searches were done at the National Centre for Biotechnology Information (NCBI) using the BLAST network service (Altschul et al., 1990).

Once clone 76 was sequenced, the library was rescreened for additional clones by DNA hybridization of plaque lifts (Sambrook, Fritsch & Maniatis, 1989). The probe used was constructed by random primer labelling of the original cDNA (excised from purified plasmid using EcoRI and Eco01091) with digoxygenin (Boehringer Mannheim). Three positive clones were isolated and sequenced.

Recombinant protein expression

Recombinant TdPI (rTdPI) was expressed as a histidine-tagged protein in *Spodoptera frujiperda* ovarian cells (SJ21; Invitrogen). The coding region of the TdPI cDNA was amplified by the polymerase chain reaction (PCR), using the forward primer

5'-GCAGGAGCTCGGCACGAG (SEQ ID NO:9)

and the reverse primer

5'-TATGGATCCCAGGTCCAGGCTCTGTTCCG (SEQ ID NO:10), thereby adding a Sac I site upstream of the start codon, and replacing the stop codon with a Bam HI site. The PCR consisted of 20 cycles with a 30-second melting step (95"Q a 30-second primer-annealing step (50° C.) and a 30-second extension step (72° C.). The PCR product was ligated between the Sac I and Ban HI sites of the pAC129.1 transfer vector (Livingstone & Jones, 1989), which was modified so that a carboxyterminal Gly-IIc-(His)$_6$ tag was added to the expressed protein. Co-transfection of SJ21 cells with the transfer vector and baculovirus (BacPak6) and amplification of recombinant virus was as described by Kitts & Possee, 1993. rTdPI was expressed in TC 100 medium (Gibco BRL) containing 10% foetal bovine serum (Sigma).

Recombinant protein purification

Sixty hours after infection of the Sf21 cells, the culture medium was collected and rTdPI was precipitated by addition of $(NH_4)_2SO_4$ (30 g per 100 ml medium). The pellet was redissolved in 50 mM sodium phosphate buffer (pH 8) containing 300 mM NaCl and 10% glycerol. rTdPI was purified using a Ni-NTA agarose (Qiagen) column, mainly according to Janknecht et al., 1991. 50 mM sodium phosphate buffer (pH 6.5) containing 300 mM NaCl and 10% glycerol was used to wash the column. The histidine-tagged protein was eluted using 200 mM imidazole in 75 mM $NaH_2PO$. Further purification was obtained by low pressure chromatography using the Biologic system (Bio-Rad) with a HiTrap SP cation exchange column (Pharmacia Biotech). The running buffer was 50 mM Hepes, pH 8, with a linear 0 to 250 mM NaCl gradient over 1 hour, the flow rate was 1 ml/min. Centricon 3 concentrators (Amicon) were used for concentration of the eluants and for buffer exchange. The purified protein was stored at −20° C. in PBS until use. Protein concentration was measured using the Bio-Rad Protein Assay and the Micro BCA Protein Assay (Pierce).

Protein electrophoresis

Sodium dodecyl sulphate-polyacrylamide gel electrophoresis (SDS-PAGE) was according to Laemmmli, 1970.

FIG. 2 shows a 15% SDS-polyacrylamide gel showing rTdPI, purified by means of metal-affinity chromatography and cation exchange. The protein in lane A had been treated with PNGase F (the ~35 kDa protein on the gel) prior to electrophoresis. Lane B contains untreated rTdPI. The molecular masses are given in kDa. Lane C contains unreduced rTdPI (no reducing agent in the loading buffer). The higher molecular weight at which unreduced rTdPI runs would normally suggest dimerization through intermolecular disulphide bridges, but mass-spectrometry places the molecular mass at about 13,500 Da, contradicting the formation of dimers.

Asparagine-linked glycosylation was studied by treating rTdPI with N-glycosidase F (PNGase F; New England BioLabs), followed by SDS-PAGE. PNGase F hydrolyses all common types of Asn-glycan chains from glycoproteins (Maley et al., 1989).

Figure 3:
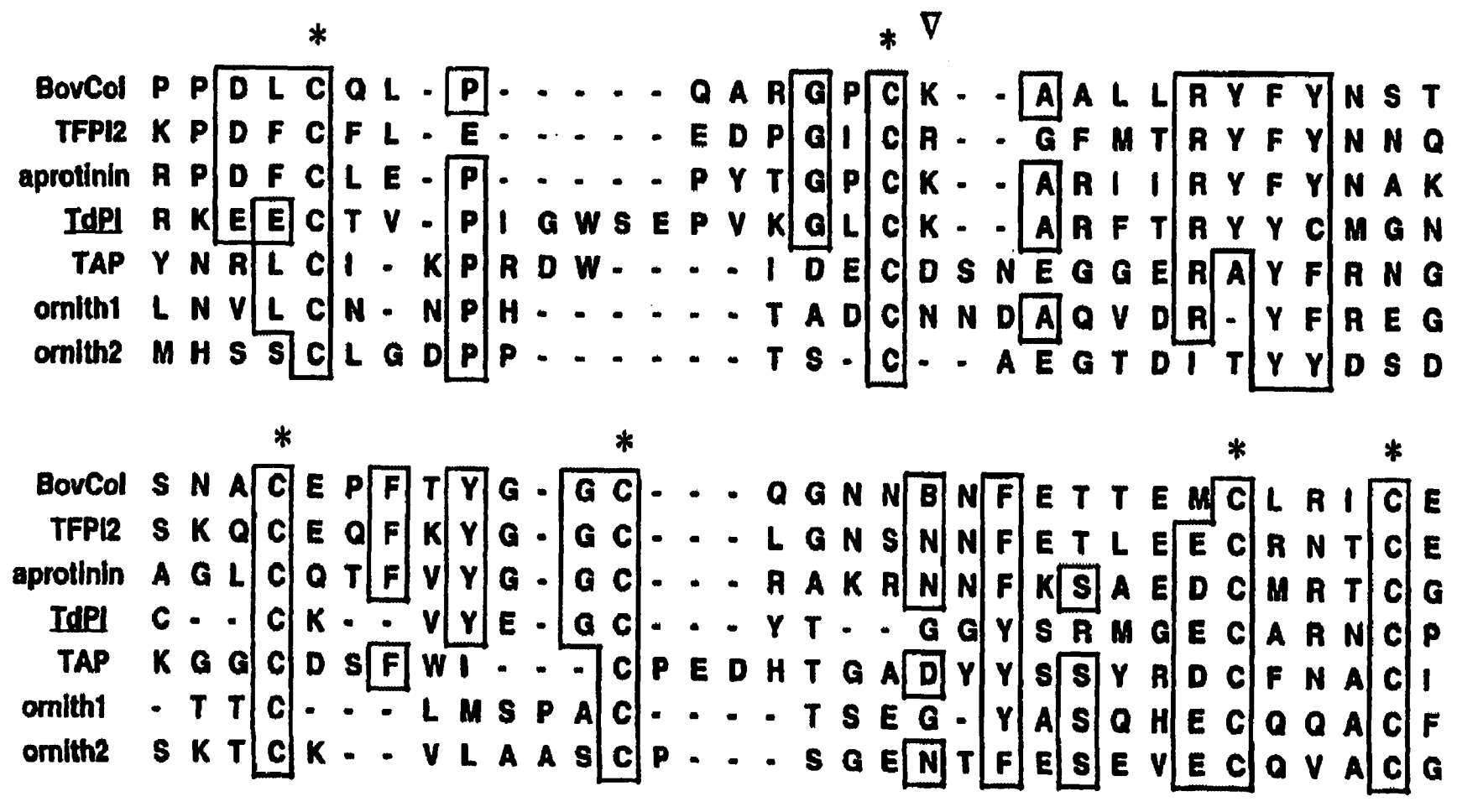

FIG. 3 shows an alignment of TdPI (SEQ ID NO:2) with Kunitz domains of the bovine colostrum "in inhibitor (SEQ ID NO:3) (BovCol; Cechova, 1976), (bovine) aprotinin (SEQ ID NO:5) (Creighton & Charles, 1987), and the rat tissue factor pathway inhibitor (SEQ ID NO:4) (TFPI-2; only the second, factor Xa-inhibiting domain is shown; Enjyoji et al., 1992). The Kunitz domains of the tick anticoagulant peptide TAP (SEQ ID NO:6) (Waxman et al., 1990) and the two domains in ornithodorin (ornithl (SEQ ID NO:7) and ornithl2 (SEQ ID NO:8); Van de Locht et al., 1996) are also included. The alignment of TdPI with the vertebrate Kunitz domains was created using GCG's "pileup" and "prettyplot" commands, choosing relatively low gap and length weights (1 and 0.03, respectively). The alignment was then modified, mainly by introducing extra gaps, so that the TAP and ornithodorin domains could be included. The modification was largely based on the alignment of the latter domains with aprotinin, as reported by Van de Locht et al., 1996. The arrow indicates the PI residue of the aprotinin binding loop. The asterisks denote the cysteines involved in disulphide-bridge formation in traditional Kunitz domains.

N-terminal sequencing

The amino-terminal sequence of rTdPI was determined at the MRC Immunochemistry Unit of the Department of Biochemistry of the University of Oxford, according to Matsudaira, 1987. Electroblotted samples were run on an Applied Biosystems 494A 'Procise' protein sequencer (Perkin-Elmer) using an Applied Biosystems 'Mini-Blott' cartridge.

Mass Spectrometry

ESI-MS was performed on a VG BioQ triple quadrapole atmospheric pressure mass spectrometer equipped with an electrospray interface operating in positive ion mode. The instrument was calibrated with horse heart myoglobin (7 pmol/$\mu$l; average molecular mass 16,951.48 Da).

Protease inhibition assays

Elastase (type 1, from porcine pancreas), α-chymotrypsin, trypsin, thrombin, plasmin, tissue kallikrein, plasma kallikrein, urokinase, aprotinin, n-succinyl-Ala-Ala-Ala-p-nitroanilide, Gly-Arg-p-nitroanilide, n-α-benzoyl-DL-Arg-p-nitroanilide and n-benzoyl-Pro-Phe-Arg-p-nitroanilide were purchased from Sigma. Factor Xa and recombinant human tryptase were from Promega and resorufin-labelled casein, soybean trypsin inhibitor, Chromozym TH and Chromozym X were obtained from Boehringer Mannheim.

Tryptase activity was measured in 96-well microplates, using n-α-benzoyl-DL-Arg-g-nitroanilide as chromogenic substrate and 50 mM HEPES pH 7.6, containing 120 mM NaCl, as reaction buffer. 50 $\mu$l buffer containing 1 $\mu$l of the tryptase stock (200 $\mu$g/ml) was combined with 50 $\mu$l of inhibitor solution (various concentrations). After a 45-minute incubation period at 37° C., 50 $\mu$l of 3 mM substrate solution was added and the increase in absorbance at 405 nM was measured using a Titertek Multiskan Plus MKII plate reader (ICN).

Other proteases were preincubated with various amounts of protease inhibitor in a total volume of 100 $\mu$l protease buffer (20 minutes; 37° C.). The residual protease activity was determined by adding the appropriate substrates (in 900 $\mu$l protease buffer) and measuring the degree of digestion. Trypsin, α-chymotrypsin, and elastase activities were measured in protease buffer A (0.1 M Tris.HCl, 10% glycerol, 10 mM $CaCl_2$, pH 8); plasmin, urokinase, kallikrein, α-thrombin and factor Xa activities were determined in protease buffer B (50 mM Tris.HCl, 0.1 mg/ml bovine serum albumin, 150 mM NaCl, 1 mM $CaCl_2$, pH 8), as described by Nakamura et al., 1987. Resorufin-labelled casein was used as a substrate for trypsin, α-chymotrypsin and plasmin, and the amount of released peptide was measured to determine protease activity (Twining, 1984). p-Nitroanilide (pNA)-substrates were used for elastase, kallikrein, urokinase, α-thrombin and factor Xa activities (n-succinyl-Ala-Ala-Ala-pNA, n-benzoyl-Pro-Phe-Arg-pNA, Gly-Arg-pNA, Chromozym TH, and Chromozym X, respectively); protease activity was measured by determining the increase in absorbance at 410 nm.

Figure 4:
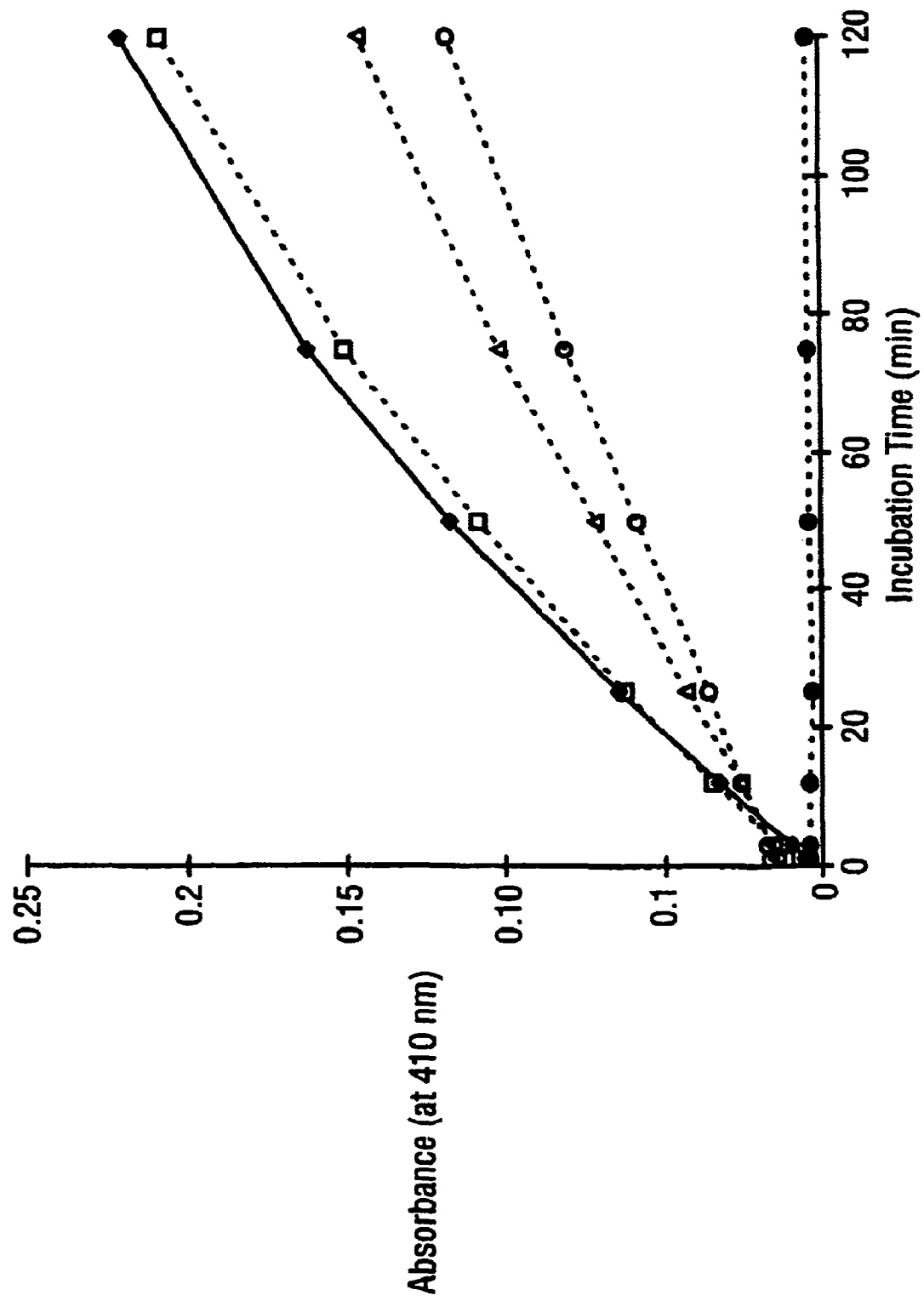
FIG. 4 shows a diagram showing the relatively weak inhibitory activity of rTdPI on tissue kallikrein.

FIG. 4 shows a diagram showing the relatively weak inhibitory activity of rTdPI on tissue kallikrein. The absorbance at 410 nm is shown at different time points after addition of 30 μg substrate (n-benzoyl-Pro-Phe-Arg-pNA) to kallikrein/antiprotease samples. 0.5 μ/ml tissue kallikrein was used per sample (1 ml final volume). The full line (♦――♦) denotes kallikrein activity in the absence of protease inhibitor. Aprotinin used at a concentration of 0.75 μM completely inhibits kallikrein activity (●――●). A ten times higher concentration of rTdPI [7.5 μM (○――○)] barely inhibits 50% of the kallikrein activity. Other concentrations of rTdPI used in the experiment were 3.75 μM (Δ――Δ) and 0.75 μM (□――□).

FIG. 5 shows the activities of plasmin (left) and trypsin (right) in the presence of increasing amounts of rTdPI as determined by measuring peptide release from resorufin-labelled casein. The peptide release in the absence of inhibitor was set to be 100%, hydrolysis in the absence of protease corresponds with 0% activity. The values for rTdPI are denoted by the open circles. To calculate the micromolar concentration of rTdPI monomers from the mg/ml data obtained with the protein assay, both the calculated molecular mass of 12 kDa (○――○) assuming no binding of Coomassie blue to the carbohydrate fraction of the glycoprotein) and the (average) molecular mass as determined by mass-spectrometry (13.5 kDa; ○――○) were used. The concentrations corresponding with a 50% plasmin inhibition are 0.097 μM for aprotinin (Δ――Δ), 0.23 μM for soybean trypsin inhibitor (■――■) 0.32 μM (○――○) and 0.43 μM (○――○) for rTdPI monomers. The values for 50% trypsin inhibition are 0.024 μM (Δ――Δ) 0.026 μM (■――■), 0.033 μM (○――○) and 0.044 μM (○――○).

Figure 6:
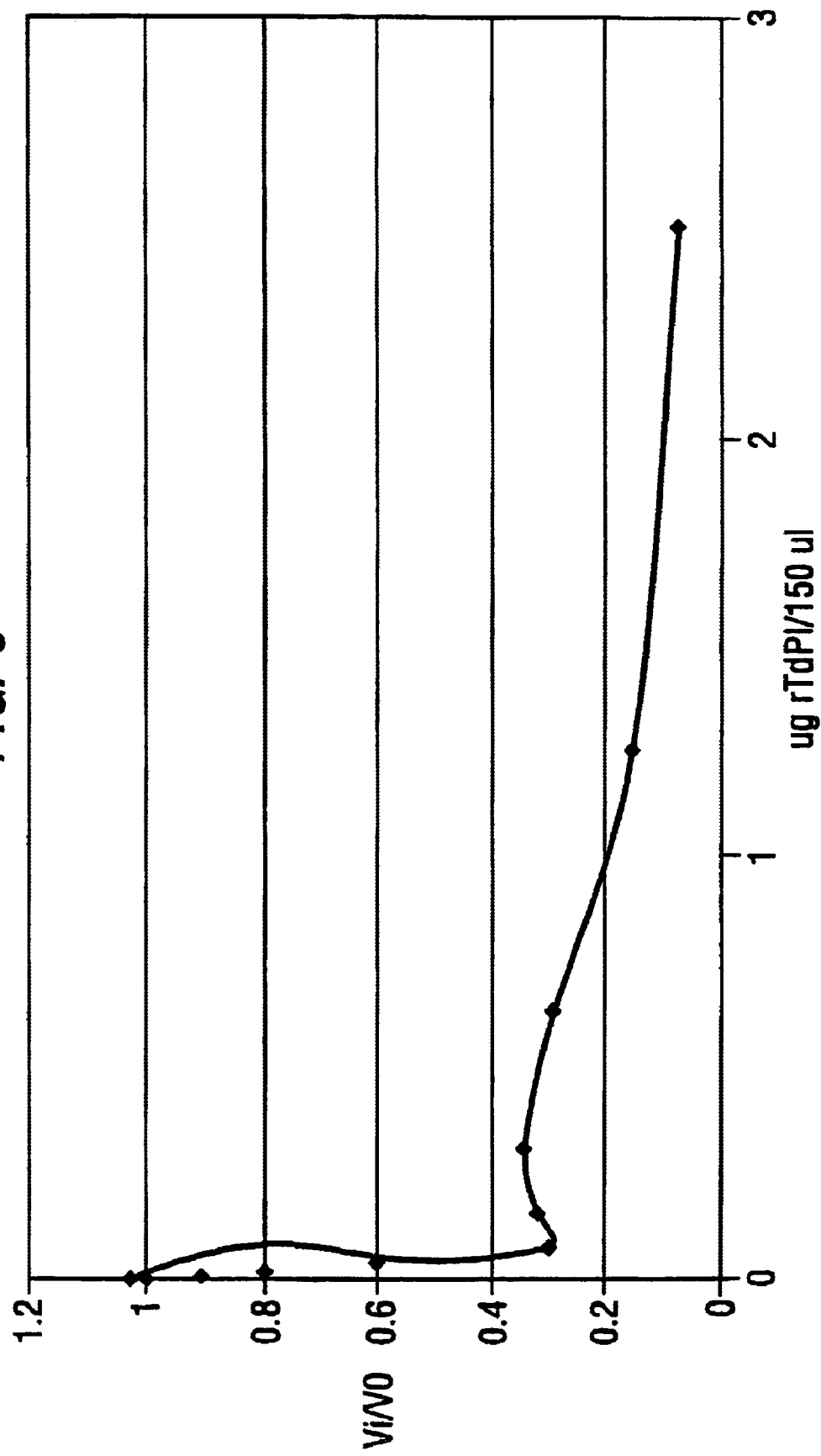
FIG. 6 shows the inhibition of recombinant human tryptase (Promega) with TdPI.

FIG. 6 shows the inhibition of recombinant human tryptase (Promega) with TdPI. Preincubation of recombinant human tryptase with increasing amounts of rTdPI quickly reduces the catalytic activity to about 33% of the activity in the absence of inhibitor ($V_0$: the velocity of substrate turnover measured without tryptase present; $V_i$: the velocity with inhibitor added).

Reverse transcriptase-polymerase chain reaction (RT-PCR)

Salivary glands were excised from unfed adult ticks, and from adult ticks that had been feeding on guinea pigs for 2, 4 and 6 days. Each tissue sample consisted of 15 pairs of glands. Total RNA was isolated from these glands using the RNAce Total Pure extraction kit (Bioline Ltd) and ⅟₃₀ of the amount obtained (the equivalent of one gland) was used as a template for RT-PCR (35 cycles), utilizing the Titan one tube RT-PCR system (Boehringer Mannheim). RT PCR was also carried out on pooled RNA from gut, gonads, accessory sex glands and malpighian tubules, taken from 2-days fed adult ticks. Whole-body homogenates of 3 days-fed larvae and 3 days-fed nymphs were submitted to the same procedure; the amount of RNA used per PCR reaction corresponded with the extract from 1 nymph or 2 larvae. The primer sequences (P1 and P2) are underlined in FIG. 1. To check whether the RT-PCR products were specifically derived from TdPI mRNA, their sizes were compared to the size of a marker that was obtained by PCR-amplification of the original plasmid DNA, using the same primers.

Figure 7:
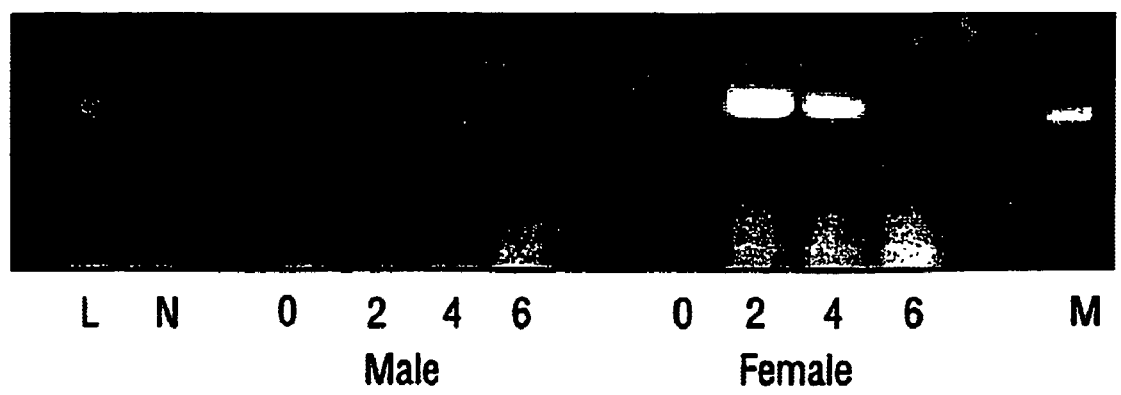
FIG. 7 shows a 1.5% agarose gel showing the RT-PCR products obtained with whole-body extracts from larvae (L) and nymphs (N), and with salivary gland extracts from adult, *R. appendiculatus* males and females.

FIG. 7 shows a 1.5% agarose gel showing the RT-PCR products obtained with whole-body extracts from larvae (L) and nymphs (N), and with salivary gland extracts from adult, *R. appendiculatus* males and females. The numbers correspond with different time points of the adult feeding stage; 0 denotes samples taken from unfed ticks; 2, 4 and 6 indicate 2, 4 and 6 days fed ticks, respectively. Lane M shows as a the molecular weight marker tee PCR product obtained with the same set of primers (FIG. 1), but using the TdPI cl)NA as a template, instead of RNA.

References

Alter S. C., Kramps J. A., Janoff A. et al. (1990) Interactions of human mast cell tryptase with biological protease inhibitors. *Archives of Biochemistry and Biophysics* 276, 26–31.

Altschul S. F., W. G., Miller W. et al. (1990) Basic local alignment search tool. *Journal of Molecular Biology* 215, 403–410.

Auerswald E. A., Morenweiser R., Sommerhoff C. P. et al. (1994) Recombinant leech-derived tryptase inhibitor, construction, production, protein chemical characterization and inhibition of HIV-1 replication. *Biological Chemistry Hoppe-Seyler* 375, 695–703.

Ausubel et al., 1991, Current Protocols in Molecular Biology, Wiley Interscience, New York.

Cechova D. (1976) Trypsin inhibitor from cow colostrum. *Methods in Enzymology* 45, 806–813.

Cregar D., Elrod K. C., Putnam D. et al. (1999) Neutrophil myeloperoxidase is a potent and selective inhibitor of mast cell tryptase. *Archives of Biochemistry and Biophysics* 366, 125–130.

Creighton T. E. & Charles I. G. (1987) Sequences of the genes and polypeptide precursors for two bovine protease inhibitors. *Journal of Molecular Biology* 194, 11–22.

Elrod K. C., Moore W. R., Abraham W. M. et al. (1997) Lactoferrin, a potent tryptase inhibitor, abolishes late-phase airway responses in allergic sheep. *American Journal of Respiratory and Critical Care Medicine* 156, 375–381.

Enjyoji K., Emi M., Mukai T. et al. (1992) cDNA cloning and expression of rat tissue factor pathway inhibitor (TFPI). *Journal of Biochemistry (Tokyo)* 111, 681–687.

Fernandez J. M. & Hoeffler J. P., eds. (1998) Gene expression systems. Using nature for the art of expression. Academic Press, San Diego, London, Boston, New York, Sydney, Tokyo, Toronto.

Program Manual for the Wisconsin Package, version 8., 575 Science Drive, Madison, Wis., USA 53711.

Goode B. L. & Feinstein S.C. (1992) "Speedprep" purification of template for double-stranded DNA-sequencing. *BioTechniques* 12, 374–375.

Janknecht R., de Martynoff G., Lou L. et al. (1991) Rapid and efficient purification of native histidine-tagged protein expressed by recombinant vaccinia virus. *Proceedings of the National Academy of Sciences USA* 88, 8972–8976.

Jones L. D., Davies C. R., Steele G. M. et al. (1988) The rearing and maintenance of ixodid and argasid ticks in the laboratory. *Animal Technology* 39, 99–106.

Kitts P. A. & Possee R. D. (1993) A method for producing recombinant baculovirus expression vectors at high frequency. *BioTechniques* 14, 810–817.

Laemmli V. K. (1970) Cleavage of structural proteins during the assembly of. the head of bacteriophage T4. *Nature* 277, 680–685.

Leon et al., (1994) *P.N.A.S. USA* 91: 3739–3743.

Liang et al., (1998) *J. Cutaneous Pathology* 25: 189–198.

Livingstone C. & Jones I. (1989) Baculovirus expression vectors with single strand capability. *Nucleic Acids Research* 17, 2366.

Maley F., Trimble R. B., Tarentino A. L. et al. (1989) Characterization of glycoproteins and their associated oligosaccharides through the use of endoglycosidases. *Analytical Biochemistry* 180,195–204.

Matsudaira P. (1987) Sequence from picomole quantities of proteins electroblotted onto polyvinylidene difluoride membranes. *Journal of Biological Chemistry* 262, 10035–10038.

Mierendorf R. C. & Pfeffer D. (1987) Direct sequencing of denatured plasmid DNA. *Methods in Enzymology* 152, 556–562.

Mühlhahn P., Czisch M., Morenweiser R. et al. (1994) Structure of leech derived tryptase inhibitor (LDTI-C) in solution. *FEBS Letters* 355, 290–296.

Nakamura T., Hirai T., Tokunaga F. et al. (1987) Purification and amino-acid sequence of kunitz-type protease inhibitor found in hemocytes of horseshoe crab (*Tachypleus tridentatus*). *Journal of Biochemistry (Tokyo)* 101,1297–1306.

Paesen G. C. & Nuttall P. A. (1996) A tick homologue of the human Ki nuclear autoantigen. *Biochimica et Biophysica Acta* 1309, 9–13.

Pohlig G., Fendrich G., Knecht R. et al. (1996) Purification, characterization and biological evaluation of recombinant leech-derived tryptase inhibitor (rLDTI) expressed at high level in the yeast *Saccharomyces cerevisiae*. *European Journal of Biochemistry* 241, 619–626.

Sambrook J., Fritsch E. F. & Maniatis T. (1989) *Molecular cloning., a laboratory manual*. pp. Pages. New York: Cold Spring Harbor Laboratory Press Sanger F. & Coulson A. R. (1975) A rapid method for determining sequences in DNA by primed synthesis with DNA polymerase. *Journal of Molecular Biology* 94, 441–448.

Schwartz L. B. (1994) tryptase a mast cell serine protease. *Methods in Enzymology* 244, 88–100.

Short J. M., Fernandez J. M., Sorge J. A. et al. (1988) Lambda-ZAP: a bacteriophage lambda expression vector with in vivo excision properties. *Nucleic Acids Research* 16, 7583–7600.

Sommerhoff C. P., Söllner C., Mentele R. et al. (1994) A Kazal-type inhibitor of human mast cell tryptase: isolation from the medical leech *Hirudo medicinalis*, characterization, and sequence analysis. *Biological Chemistry Hoppe-Seyler* 375, 685–694.

Spector, et al., 1998, Cells, a laboratory manual; Cold Spring Harbor Laboratory Press., New York.

Stubbs M. T., Morenweiser R., Stüzebecher J. et al. (1997) The three-dimensional structure of recombinant leech-derived tryptase inhibitor in complex with trypsin. Implications for the structure of human mast cell tryptase and its inhibition. *Journal of Biological Chemistry* 272, 19931–19937.

Towbin et al., (1979) *P.N.A.S. USA* 76: 4350–4354.

Twining S. S. (1984) Fluorescein isothiocyanate-labeled casein assay for proteolytic enzymes. *Analytical Biochemistry* 143, 30–34.

Van de Locht A., Stubbs M. T., Bode W. et al. (1996) The ornithodorin-thrombin crystal structure, a key to the TAP enigma? *EMBO Journal* 15, 6011–6017.

Waxman L., Smith D. E., Arcuri K. E. et al. (1990) Tick anticoagulant peptide (TAP) is a novel inhibitor of blood coagulation factor Xa. *Science* 248, 593–596.

What is claimed is:

1. A recombinant protein comprising SEQ ID NO: 2 or a protein fragment thereof wherein said fragment consists of a fragment of SEQ ID NO:2 that inhibits tryptase with a Ki of less than $1\times10^{-6}$ M.

2. A recombinant protein or protein fragment according to claim 1, that functions as an inhibitor of human mast cell tryptase.

3. A fusion protein wherein said recombinant protein or said protein fragment according to claim 1 has been genetically or chemically fused to one or more peptides or polypeptides.

4. A recombinant protein or protein fragment according to claim 1 that is bound to a support, such as a resin.

5. A recombinant protein or protein fragment according to claim 1 that inhibits tryptase with a Ki of less than $1\times10^{-7}$ M, preferably less than $2\times10^{-8}$ M, most preferably less than $1\times10^{-9}$ M.

6. A recombinant protein or protein fragment according to claim 1 that inhibits catalytic tryptase activity.

7. A recombinant protein or protein fragment according to claim 1 which inhibits mast cell tryptase.

8. A recombinant protein or protein fragment according to claim 1 that is derived from a tick.

9. A recombinant protein or protein fragment according to claim 8 that is derived from the tick *Rhipicephalus appendiculatus*.

10. An anti-tryptase agent comprising a recombinant protein or protein fragment according to claim 1.

* * * * *

SEQUENCE LISTING

<160> NUMBER OF SEQ ID NOS: 10

<210> SEQ ID NO 1
<211> LENGTH: 490
<212> TYPE: DNA
<213> ORGANISM: Rhicephalus appendiculatus

<400> SEQUENCE: 1

```
gaaacctcat gggccgcact accctaatcg tcgccatcgt gctggtggct ttcgttgcaa      60
gcacactagg aaatgcctac cctaaagtgg aagaaagacg taacaggcct aattgggatt     120
ttgggaaaag gaaagaagag tgtaccgttc ctattggttg gagcgaacca gtaaaagggc     180
tttgcaaggc tagatttact aggtattact gcatgggaa ctgttgcaag gtatacgaag     240
gctgctacac aggaggctat tccagaatgg gtgaatgcgc gagaaattgt cccggcttca     300
aaagaccgac accagggttc agaccacggc acggactaga gaacggaaca gagcctggac     360
cttgaaacct cagataataa ttctccgaag acctcgatta tttcaccatg aggccgtttt     420
tttttccaca ataaaagcgg acaaggagaa catacatcat actgaaataa aataagaaac     480
caaaaaaaaa                                                           490
```

<210> SEQ ID NO 2
<211> LENGTH: 118
<212> TYPE: PRT
<213> ORGANISM: Rhicephalus appendiculatus

<400> SEQUENCE: 2

```
Met Gly Arg Thr Thr Leu Ile Val Ala Ile Val Leu Val Ala Phe Val
 1               5                  10                  15
```

```
Ala Ser Thr Leu Gly Asn Ala Tyr Pro Lys Val Glu Glu Arg Arg Asn
         20                  25                  30

Arg Pro Asn Trp Asp Phe Gly Lys Arg Lys Glu Glu Cys Thr Val Pro
         35                  40                  45

Ile Gly Trp Ser Glu Pro Val Lys Gly Leu Cys Lys Ala Arg Phe Thr
 50                  55                  60

Arg Tyr Tyr Cys Met Gly Asn Cys Cys Lys Val Tyr Glu Gly Cys Tyr
 65                  70                  75                  80

Thr Gly Gly Tyr Ser Arg Met Gly Glu Cys Ala Arg Asn Cys Pro Gly
                 85                  90                  95

Phe Lys Arg Pro Thr Pro Gly Phe Arg Pro Arg His Gly Leu Glu Asn
             100                 105                 110

Gly Thr Glu Pro Gly Pro
            115

<210> SEQ ID NO 3
<211> LENGTH: 56
<212> TYPE: PRT
<213> ORGANISM: Bos taurus

<400> SEQUENCE: 3

Pro Pro Asp Leu Cys Gln Leu Pro Gln Ala Arg Gly Pro Cys Lys Ala
 1               5                  10                  15

Ala Leu Leu Arg Tyr Phe Tyr Asn Ser Thr Ser Asn Ala Cys Glu Pro
             20                  25                  30

Phe Thr Tyr Gly Gly Cys Gln Gly Asn Asn Asx Asn Phe Glu Thr Thr
             35                  40                  45

Glu Met Cys Leu Arg Ile Cys Glu
 50                  55

<210> SEQ ID NO 4
<211> LENGTH: 56
<212> TYPE: PRT
<213> ORGANISM: Rattus norvegicus

<400> SEQUENCE: 4

Lys Pro Asp Phe Cys Phe Leu Glu Glu Asp Pro Gly Ile Cys Arg Gly
 1               5                  10                  15

Phe Met Thr Arg Tyr Phe Tyr Asn Asn Gln Ser Lys Gln Cys Glu Gln
             20                  25                  30

Phe Lys Tyr Gly Gly Cys Leu Gly Asn Ser Asn Asn Phe Glu Thr Leu
             35                  40                  45

Glu Glu Cys Arg Asn Thr Cys Glu
 50                  55

<210> SEQ ID NO 5
<211> LENGTH: 56
<212> TYPE: PRT
<213> ORGANISM: Bos taurus

<400> SEQUENCE: 5

Arg Pro Asp Phe Cys Leu Glu Pro Pro Tyr Thr Gly Pro Cys Lys Ala
 1               5                  10                  15

Arg Ile Ile Arg Tyr Phe Tyr Asn Ala Lys Ala Gly Leu Cys Gln Thr
             20                  25                  30

Phe Val Tyr Gly Gly Cys Arg Ala Lys Arg Asn Asn Phe Lys Ser Ala
             35                  40                  45
```

```
Glu Asp Cys Met Arg Thr Cys Gly
 50                  55
```

<210> SEQ ID NO 6
<211> LENGTH: 60
<212> TYPE: PRT
<213> ORGANISM: Ornithodoros moubata

<400> SEQUENCE: 6

```
Tyr Asn Arg Leu Cys Ile Lys Pro Arg Asp Trp Ile Asp Glu Cys Asp
 1               5                  10                  15

Ser Asn Glu Gly Gly Glu Arg Ala Tyr Phe Arg Asn Gly Lys Gly Gly
             20                  25                  30

Cys Asp Ser Phe Trp Ile Cys Pro Glu Asp His Thr Gly Ala Asp Tyr
         35                  40                  45

Tyr Ser Ser Tyr Arg Asp Cys Phe Asn Ala Cys Ile
 50                  55                  60
```

<210> SEQ ID NO 7
<211> LENGTH: 51
<212> TYPE: PRT
<213> ORGANISM: Ornithodoros moubata

<400> SEQUENCE: 7

```
Leu Asn Val Leu Cys Asn Asn Pro His Thr Ala Asp Cys Asn Asn Asp
 1               5                  10                  15

Ala Gln Val Asp Arg Tyr Phe Arg Glu Gly Thr Thr Cys Leu Met Ser
             20                  25                  30

Pro Ala Cys Thr Ser Glu Gly Tyr Ala Ser Gln His Glu Cys Gln Gln
         35                  40                  45

Ala Cys Phe
     50
```

<210> SEQ ID NO 8
<211> LENGTH: 54
<212> TYPE: PRT
<213> ORGANISM: Ornithodoros moubata

<400> SEQUENCE: 8

```
Met His Ser Ser Cys Leu Gly Asp Pro Pro Thr Ser Cys Ala Glu Gly
 1               5                  10                  15

Thr Asp Ile Thr Tyr Tyr Asp Ser Asp Ser Lys Thr Cys Lys Val Leu
             20                  25                  30

Ala Ala Ser Cys Pro Ser Gly Glu Asn Thr Phe Glu Ser Glu Val Glu
         35                  40                  45

Cys Gln Val Ala Cys Gly
 50
```

<210> SEQ ID NO 9
<211> LENGTH: 18
<212> TYPE: DNA
<213> ORGANISM: Artificial Sequence
<220> FEATURE:
<223> OTHER INFORMATION: PCR Primer

<400> SEQUENCE: 9
gcaggagctc ggcacgag                                                      18

<210> SEQ ID NO 10
<211> LENGTH: 29
<212> TYPE: DNA

```
<213> ORGANISM: Artificial Sequence
<220> FEATURE:
<223> OTHER INFORMATION: PCR Primer

<400> SEQUENCE: 10
tatggatccc aggtccaggc tctgttccg                                        29
```